US010750297B2

(12) United States Patent
Jinton et al.

(10) Patent No.: US 10,750,297 B2
(45) Date of Patent: Aug. 18, 2020

(54) BONE ANCHOR FIXTURE FOR A MEDICAL PROSTHESIS

(71) Applicants: Lars Jinton, Mölndal (SE); Erik Holgersson, Gothenburg (DE); Peter Elmberg, Kållered (SE)

(72) Inventors: Lars Jinton, Mölndal (SE); Erik Holgersson, Gothenburg (DE); Peter Elmberg, Kållered (SE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 15/830,616

(22) Filed: Dec. 4, 2017

(65) Prior Publication Data

US 2018/0220245 A1   Aug. 2, 2018

Related U.S. Application Data

(63) Continuation of application No. 14/922,604, filed on Oct. 26, 2015, now Pat. No. 9,838,807, which is a
(Continued)

(51) Int. Cl.
*A61B 17/86* (2006.01)
*H04R 25/00* (2006.01)
*A61C 8/00* (2006.01)

(52) U.S. Cl.
CPC ......... *H04R 25/606* (2013.01); *A61B 17/863* (2013.01); *A61B 17/8615* (2013.01);
(Continued)

(58) Field of Classification Search
CPC .......................... H04R 25/606; A61B 17/8615
See application file for complete search history.

(56) References Cited

U.S. PATENT DOCUMENTS

| 2,016,610 A | 10/1935 | Moeller |
| 2,347,567 A * | 4/1944 | Kresse ............... A61C 8/0022 |
| | | 424/487 |

(Continued)

FOREIGN PATENT DOCUMENTS

| EP | 0996391 B1 | 2/2004 |
| KR | 20120000235 A | 1/2012 |

(Continued)

OTHER PUBLICATIONS

Extended European Search Report for European Application No. 08782157.5 dated Jan. 2, 2013.
(Continued)

*Primary Examiner* — Christian A Sevilla
(74) *Attorney, Agent, or Firm* — Pilloff Passino & Cosenza LLP; Martin J. Cosenza (57) ABSTRACT

A screw-shaped anchoring fixture for anchoring a prosthesis in the skull bone. The anchoring fixture comprises a main body configured to be implanted into the bone and a flange configured to function as a stop to prevent the main body from completely penetrating through the bone. The main body comprises a distal tapered apical portion, a first portion, and a second portion. The inner diameter of the second portion is greater than the inner diameter of the first portion. The method for inserting the anchoring fixture includes providing the anchoring fixture, drilling a hole, and inserting the anchoring fixture into the hole until the flange contacts the skull bone, wherein the hole has a diameter that is greater than the inner diameter of the first portion and less than the outer diameter of the second portion.

61 Claims, 2 Drawing Sheets

Related U.S. Application Data continuation of application No. 12/177,083, filed on Jul. 21, 2008, now Pat. No. 9,173,042.

(60) Provisional application No. 60/951,169, filed on Jul. 20, 2007, provisional application No. 60/951,163, filed on Jul. 20, 2007.

(52) U.S. Cl.
CPC .......... *A61C 8/0025* (2013.01); *A61C 8/0066* (2013.01); *A61C 8/0069* (2013.01); *H04R 2460/13* (2013.01)

(56) References Cited

U.S. PATENT DOCUMENTS

| | | | |
|---|---|---|---|
| 4,025,964 A | 5/1977 | Owens | |
| 4,498,461 A * | 2/1985 | Hakansson | H04R 25/606 |
| | | | 600/25 |
| D294,295 S | 2/1988 | Branemark | |
| 4,738,623 A | 4/1988 | Driskell | |
| 4,904,233 A | 2/1990 | Hakansson et al. | |
| 4,917,555 A | 4/1990 | Taubert | |
| 4,936,317 A | 6/1990 | MacGregor | |
| 4,998,461 A | 3/1991 | Ishiwata et al. | |
| 5,019,078 A | 5/1991 | Perren et al. | |
| 5,135,395 A | 8/1992 | Marlin | |
| 5,269,685 A * | 12/1993 | Jorneus | A61C 8/0022 |
| | | | 433/173 |
| 5,588,883 A | 12/1996 | Hattori | |
| 5,653,710 A | 8/1997 | Harle | |
| 5,720,766 A | 2/1998 | Zang et al. | |
| 5,735,790 A * | 4/1998 | Håkansson | H04R 25/606 |
| | | | 600/25 |
| 5,769,630 A | 6/1998 | Hoffman | |
| 5,833,463 A | 11/1998 | Hurson | |
| 5,885,079 A * | 3/1999 | Niznick | A61C 8/0022 |
| | | | 433/174 |
| 5,961,329 A | 10/1999 | Stucki-McCormick | |
| 6,030,162 A | 2/2000 | Huebner | |
| 6,086,303 A | 7/2000 | Fluckiger | |
| 6,183,255 B1 | 2/2001 | Oshida | |
| 6,468,277 B1 * | 10/2002 | Justin | A61B 17/863 |
| | | | 606/304 |
| 6,474,991 B1 | 11/2002 | Hansson | |
| 6,604,945 B1 | 8/2003 | Jones | |
| 6,643,378 B2 | 11/2003 | Schumaier | |
| 6,669,701 B2 | 12/2003 | Stiener et al. | |
| 6,840,919 B1 | 1/2005 | Hakansson | |
| 6,896,517 B1 | 5/2005 | Bjorn et al. | |
| 6,953,463 B2 | 10/2005 | West, Jr. | |
| 6,981,873 B2 | 1/2006 | Choi et al. | |
| 7,065,223 B2 | 6/2006 | Westerkull | |
| 7,074,222 B2 | 7/2006 | Westerkull | |
| 7,116,794 B2 | 10/2006 | Westerkull | |
| 7,806,693 B2 | 10/2010 | Hurson | |
| D634,186 S | 3/2011 | Kemper | |
| 8,016,593 B2 | 9/2011 | Hall | |
| 8,170,252 B2 | 5/2012 | Parker et al. | |
| 8,377,106 B2 | 2/2013 | Branemark et al. | |
| 9,931,184 B2 | 4/2018 | Hall | |
| 2003/0176866 A1 * | 9/2003 | Westerkull | A61F 2/141 |
| | | | 606/312 |
| 2004/0032962 A1 | 2/2004 | Westerkull | |
| 2004/0152047 A1 | 8/2004 | Odrich et al. | |
| 2004/0210103 A1 | 10/2004 | Westerkull | |
| 2004/0228705 A1 | 11/2004 | Baer et al. | |
| 2005/0106534 A1 | 5/2005 | Gahlert | |
| 2005/0153261 A1 | 7/2005 | Chang | |
| 2005/0248158 A1 | 11/2005 | Westerkull | |
| 2005/0249366 A1 | 11/2005 | Westerkull | |
| 2005/0250074 A1 | 11/2005 | Lang et al. | |
| 2005/0287497 A1 | 12/2005 | Carter | |
| 2006/0050913 A1 * | 3/2006 | Westerkull | H04R 25/606 |
| | | | 381/326 |
| 2006/0056649 A1 | 3/2006 | Schumaier | |
| 2006/0093175 A1 * | 5/2006 | Westerkull | H04R 25/606 |
| | | | 381/326 |
| 2006/0126874 A1 | 6/2006 | Westerkull | |
| 2006/0172257 A1 | 8/2006 | Niznick | |
| 2006/0195099 A1 | 8/2006 | Bottlang | |
| 2006/0211910 A1 | 9/2006 | Westerkull | |
| 2007/0009853 A1 | 1/2007 | Pitulia | |
| 2007/0053536 A1 | 3/2007 | Westerkull | |
| 2007/0059666 A1 | 3/2007 | Zickman et al. | |
| 2007/0147973 A1 | 6/2007 | Laan | |
| 2008/0032264 A1 | 2/2008 | Hall | |
| 2009/0023109 A1 | 1/2009 | Jinton et al. | |
| 2009/0082817 A1 | 3/2009 | Jinton et al. | |
| 2010/0240010 A1 | 9/2010 | Holmstrom | |
| 2010/0249784 A1 | 9/2010 | Andersson | |
| 2010/0286776 A1 | 11/2010 | Andersson | |
| 2011/0195380 A1 | 8/2011 | Giomo | |
| 2012/0143251 A1 | 6/2012 | Green et al. | |
| 2015/0215696 A1 | 7/2015 | Bjorn et al. | |

FOREIGN PATENT DOCUMENTS

| | | |
|---|---|---|
| SE | 531177 C2 | 1/2009 |
| WO | 9205745 A1 | 4/1992 |
| WO | 9619950 A1 | 7/1996 |
| WO | 9855049 A1 | 12/1998 |
| WO | 9923971 A1 | 5/1999 |
| WO | 0193634 A1 | 12/2001 |
| WO | 0193645 A1 | 12/2001 |
| WO | 0209622 A1 | 2/2002 |
| WO | 2004012622 A1 | 2/2004 |
| WO | 2004045432 A1 | 6/2004 |
| WO | 2004058091 A1 | 7/2004 |
| WO | 2004093401 A1 | 10/2004 |
| WO | 2004098442 A1 | 11/2004 |
| WO | 2004105650 A1 | 12/2004 |
| WO | 2005000391 A1 | 1/2005 |
| WO | 2006052527 A2 | 5/2006 |
| WO | 2006065205 A1 | 6/2006 |
| WO | 2009015102 A1 | 1/2009 |
| WO | 2009015103 A1 | 1/2009 |

OTHER PUBLICATIONS

Extended European Search Report for European Application No. 08782159.1 dated Jan. 3, 2013.
Sjostrom et al., "Monitoring of implant stability in grafted bone using resonance frequency analysis—A clinical study from implant placement to 6 months of loading", Jan. 2005, pp. 45-51, vol. 34, issue 1.
http://www.merriam-webster.com/dictionary/tapered, Retrieved Apr. 10, 2012.
http://www.merriam-webster.com/dictionary/apical, Retrieved Apr. 10, 2012.
http://www.merriam-webster.com/dictionary/portion, Retrieved Apr. 10, 2012.
Written Opinion for PCT/US2008/070679, dated Oct. 27, 2008.
International Preliminary Report on Patentability for PCT/US2008/070681, dated Aug. 21, 2009.
Written Opinion for PCT/US2008/070681, dated Dec. 15, 2008.
Mats Thomsson et al., "A retrospective case series evaluating Branemark BioHelix implants placed in a specialist private practice following 'conventional' procedures. One-year results after placement," Eur J Oral Implantol., Oct. 2008, pp. 229-234, vol. 1, No. 3.
Oticon Medical AB et al., "Defendants' Invalidity Contentions," U.S. District Court for the District of New Jersey, Case No. 3:18-cv-06684, filed Oct. 9, 2018.
Cochlear Ltd., "Cochlear Ltd.'s Responses to Invalidity Contentions," U.S. District Court for the District of New Jersey, Case No. 3:18-cv-06684, filed Oct. 15, 2018.
Cochlear Ltd., "Plaintiff Cochlear Ltd.'s Opening Brief Regarding Claim Construction," U.S. District Court for the District of New Jersey, Case No. 3:18-cv-06684, filed Jan. 18, 2019.

(56) References Cited

OTHER PUBLICATIONS

Cochlear Ltd., "Declaration of Mark E. Rentschler, Ph.D. In Support of Plaintiff's Opening Brief Regarding Claim Construction," U.S. District Court for the District of New Jersey, Case No. 3:18-v-06684, filed Jan. 18, 2019.
Oticon Medical AB et al., "Oticon Medical's Opening Claim Construction Brief," U.S. District Court for the District of New Jersey, Case No. 3:18-cv-06684, filed Jan. 18, 2019.
Oticon Medical AB et al., "Expert Declaration of Dr. Wilson Hayes in Support of Oticon Medical AB and Oticon Medical LLC's Claim Construction Brief," U.S. District Court for the District of New Jersey, Case No. 3:18-cv-06684, filed Jan. 18, 2019.
Oticon Medical AB et al., "Oticon Medical's Rebuttal Claim Construction Brief," U.S. District Court for the District of New Jersey, Case No. 3:18-cv-06684, filed Mar. 1, 2019.
Cochlear Ltd., "Plaintiff Cochlear Ltd.'s Responsive Brief Regarding Claim Construction," U.S. District Court for the District of New Jersey, Case No. 3:18-cv-06684, filed Mar. 1, 2019.
Cochlear Ltd., "Supplemental Declaration of Mark. E. Rentschler, PH.D. In Support of Plaintiff Cochlear Ltd.'s Claim Constructions," U.S. District Court for the District of New Jersey, Case No. 3:18-cv-06684, filed Mar. 1, 2019.
Oticon Medical AB et al., "Oticon Medical's Supplemental Submission on Claim Construction," U.S. District Court for the District of New Jersey, Case No. 3:18-cv-06684, filed Jul. 10, 2019.
Cochlear Ltd., "Plaintiff Cochlear Ltd.'s Supplemental Brief Regarding Claim Construction," U.S. District Court for the District of New Jersey, Case No. 3:18-cv-06684, filed Jul. 10, 2019.
Cochlear Ltd., "Cochlear Ltd.'s Amended Responses to Invalidity Contentions," U.S. District court for the District of New Jersey, Case No. 3:18-cv-06684, filed Aug. 9, 2019.
Oticon Medical AB et al, "Petition for Inter Partes Review of of U.S. Pat. No. 9,838,807," IPR2019-00975, filed Apr. 15, 2019.
E.M. Lillie et al., "Evaluation of Skull Cortical Thickness Changes With Age and Sex From Computed Tomography Scans," Journal of Bone and Mineral Research, vol. 31(2), pp. 299-307 (Feb. 2016).
J.J. Wazen et al., "Long-Term Results With the Titanium Bone-Anchored Hearing Aid: The U.S. Experience," The American Journal of Otology, vol. 19, pp. 737-741 (1998).
M. Chasin et al., "Current Trends in Implantable Hearing Aids," Trends in Amplification, vol. 2, No. 3, pp. 84-107 (1997).
A. Tjellström et al., "Osseointegrated Titanium Implants in the Temporal Bone," The American Journal of Otology, vol. 2, No. 4, pp. 304-310 (1998).
L. Rasmusson et al., "Effects of Implant Design and Surface on Bone Regeneration and Implant Stability: An Experimental Study in the Dog Mandible," Clinical Implant Dentistry and Related Research, vol. 3, No. 1, pp. 2-8 (2001).
Cochlear Limited, "Patent Owner's Preliminary Response," IPR2019-00975, filed Jul. 20, 2019.
Christine A. den Besten et al., "Stability, Survival, and Tolerability of an Auditory Osseointegrated Implant for Bone Conduction Hearing: Long-Term Follow-Up of a Randomized Controlled Trial," Otology & Neurotology, vol. 37, pp. 1077-1083 (2016).
Soren Foghsgaard et al., "A New Wide-Diameter Bone-Anchored Hearing Implant—Prospective 1-Year Data on Complications, Implant Stability, and Survival," Otology & Neurotology, vol. 35, pp. 1238-1241 (2014).
Rik C. Nelissen et al., "Stability, Survival, and Tolerability of a 4.5-mm-wide Bone-anchored Hearing Implant: 6-month Data from a Randomized Controlled Clinical Trial," Eur. Arch. Otorhinolaryngol., DOI 10.1007/s00405-015-3593-x (2015).
Cochlear Limited, "Patent Owner's Updated Exhibit List," IPR2019-00975, filed Jan. 13, 2020.
Cochlear Limited, "Patent Owner's Updated Exhibit List," IPR2019-00975, filed Jan. 23, 2020.
"Joint Redacted Patent Owner's Response," IPR2019-00975, filed Jan. 23, 2020.

* cited by examiner

BONE ANCHOR FIXTURE FOR A MEDICAL PROSTHESIS

CROSS-REFERENCE TO RELATED APPLICATIONS

The present application is a Continuation application of U.S. patent application Ser. No. 14/922,604, filed Oct. 26, 2015, naming Lars Jinton as an inventor, which is a Continuation application of U.S. patent application Ser. No. 12/177,083, filed Jul. 21, 2008, now U.S. Pat No. 9,173,042, which claims the benefit of U.S. Provisional Application No. 60/951,163, filed Jul. 20, 2007, and U.S. Provisional Application No. 60/951,169, filed Jul. 20, 2007.The entire contents of these applications are incorporated herein by reference in their entirety.

BACKGROUND

Filed of the Invention

The present invention relates generally to hearing devices and, more particularly, to anchoring elements for bone anchored hearing devices.

Related Art

For persons who cannot benefit from traditional, air conduction hearing aids there are other types of hearing aids on the market commonly referred to as bone anchored hearing aids. Bone anchored hearing aids mechanically transmit sound information to a person's inner ear via the skull bone by means of a vibrator. Such hearing aid devices are typically connected to a percutaneous implant in the form of a titanium screw implanted in the skull bone behind the external ear so that sound is transmitted via the skull bone to the cochlea (inner ear). This enables the hearing aid to be effective regardless of whether there is disease or damage in the middle ear. Moreover, penetration of the skin makes the vibratory transmission very efficient.

Bone anchored hearing aids were initially developed to rehabilitate certain types of hearing-impaired patients. They may also be utilized for other indications such as stuttering and for certain non-medical applications. A bone anchored hearing aid may be connected to an implant by means of a bayonet coupling, a snap-in coupling, a magnetic coupling or the like. One example of this type of hearing aid device is the BAHA® bone anchored hearing aid, described in U.S. Pat. No. 4,498,461 and commercially available from Cochlear Bone Anchored Solutions AB (previously Entific Medical Systems AB) in Göteborg, Sweden.

The implant connecting the hearing aid to the skull generally comprises two components: a bone attachment piece that is attached or implanted directly into the skull bone and a skin penetrating piece coupled to the bone attachment piece. The reason for this two-piece design is that installation of the implant is occasionally performed in two steps. In the first step, the bone attachment piece is installed and the surrounding issue is allowed to heal for a period of time that may last up to a few months. In the second step, the skin penetrating piece is coupled to the bone attachment piece. In the event that the skin penetrating piece becomes damaged, it may be replaced without removing the anchoring fixture from the skull. Moreover, the hearing aid may be changed or upgraded if necessary, without removing the bone attachment piece from the skull.

Although conventional fixtures normally provide a certain degree of osseo-integration, a more effective integration between the implant screw and the skull bone is desired, for example, for patients having impaired bone quality. Moreover, loading of the implant at an earlier stage would also be desired.

SUMMARY

In one embodiment, an anchoring fixture for anchoring a prosthesis to a skull bone is disclosed. The anchoring fixture comprises a main body configured to be implanted into the skull bone. The main body further comprises a distal tapered apical portion and a first portion adjacent to the distal tapered apical portion. The main body also comprises a second portion adjacent to the first portion. The first portion has a first inner diameter and the second portion has a second inner diameter that is greater than the first inner diameter. This configuration provides compression in the radial direction on the skull bone to improve the initial stability of the anchoring fixture.

In another embodiment, an anchoring fixture for anchoring a prosthesis to a skull bone is disclosed. The anchoring fixture comprises a main body configured to be implanted into the skull bone and a flange. The main body further comprises a distal tapered apical portion and a first threaded portion having a first diameter adjacent to the distal apical portion and an adjacent second threaded portion having a second diameter. The second diameter is greater than the first diameter. The flange is adjacent to the second threaded portion, the flange comprising a planar bottom surface adapted to rest on top of the skull bone when the main body is implanted into the skull bone.

In yet another embodiment, an anchoring fixture for anchoring a prosthesis to a skull bone is disclosed. The anchoring fixture comprises an implantation means for securing the anchoring fixture onto the skull bone without completely penetrating through the skull bone. The implantation means comprises a compression means for exerting a compression onto the skull bone in a radial direction to stabilize the fixture in the skull bone.

In a further embodiment, a method for installing the anchoring fixture into a skull bone is disclosed. The method comprises providing an anchoring fixture, drilling a hole into the skull bone and inserting the anchoring fixture in the hole until the flange contacts the skull bone, wherein the hole has a diameter that is greater than the inner diameter of the first portion and less than the outer diameter of the second portion. In one aspect of the embodiment, the inserting step comprises screwing the anchoring fixture into the skull bone.

BRIEF DESCRIPTION OF THE DRAWINGS

Embodiments of the present invention are described herein with reference to the accompanying drawings, in which.

Like numerals refer to like parts throughout the several views of the drawings.

DETAILED DESCRIPTION OF THE INVENTION

Aspects of the various embodiments disclosed herein are generally directed to providing screw-shaped anchoring fixtures configured to be anchored in the comparatively thin skull bone and having a certain compressive ability in the radial direction to improve the initial stability of the fixture.

In one embodiment, the anchoring fixture has a main body configured to be inserted in the skull bone and a flange configured to prevent the fixture from completely penetrating through the skull bone. The main body comprises a first and second substantially cylindrical portion. The first portion comprises a screw thread having a first inner diameter and the second portion is adjacent to the flange and has a second inner diameter that is greater than the first inner diameter. Preferably, the second portion has at least one groove extending around the periphery of the cylindrical portion. The groove may have a bottom diameter exceeding the first inner diameter of the screw thread. Preferably, the groove forms a second screw thread having an inner diameter exceeding the inner diameter of the first, main screw thread. The surface of at least the first portion of the main body may be modified to increase the surface roughness.

In another embodiment, a method for inserting the anchoring fixture is disclosed. In accordance with one aspect of this embodiment, a drill may be used to drill a hole in the skull bone before installing the anchoring fixture. The drill creates a hole in the skull bone having a diameter which is larger than the inner diameter of the screw thread of the first cylindrical portion, but less than the outer diameter of the second cylindrical portion. When the fixture is inserted into the drilled hole, the wider second portion of the fixture, i.e. the portion next to the flange, provides a certain compression to the bone, specifically the cortical bone, in the radial direction of the hole.

Figure 1:
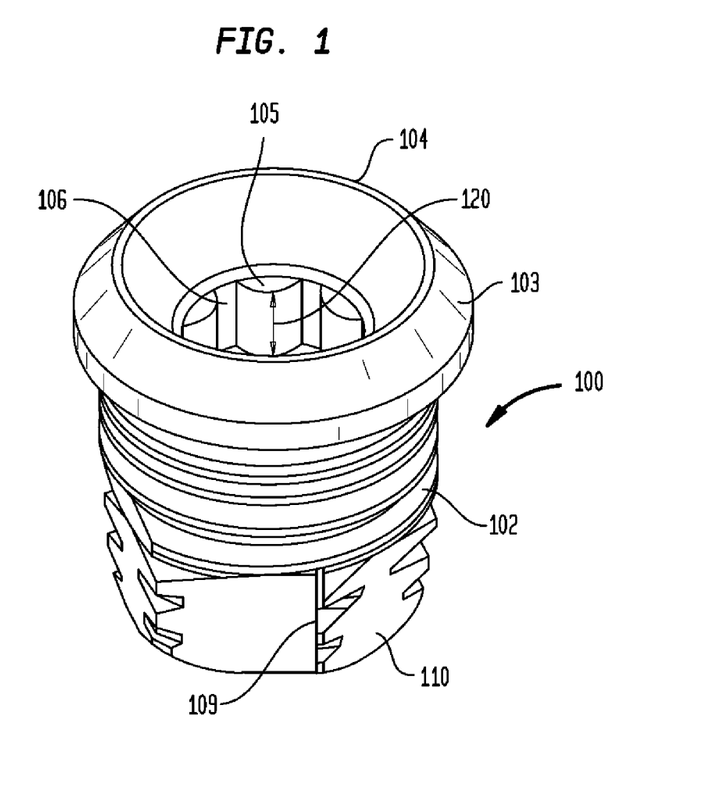
FIG. 1 is a perspective view of an anchoring element in accordance with one embodiment of the anchoring fixture.

Embodiments of the bone anchored coupling apparatus will be described below with reference to the accompanying drawings. FIG. 1 illustrates an example of a screw-shaped anchoring fixture 100 in accordance with one embodiment. Fixture 100 is preferably made of any biocompatible material that has a known ability to integrate with the surrounding bone tissue, a phenomenon commonly referred to as osseointegration. In one embodiment, fixture 100 is made of titanium. Fixture 100 has a main body 102 configured to be implanted into the skull bone, a flange 103 configured to serve as a stop to prevent fixture from penetrating through the skull bone, and a tool engaging socket 104 in the form of an internal grip section 105 for easy lifting and handling of fixture 100. The geometrical configuration of the internal grip section may be configured in a manner that allows for engagement with an insertion tool. In accordance with one aspect, the geometric configuration may be in the form of a hex, multi-lobed surfaces, slots or grooves. As shown in FIG. 1 a number of lobe-shaped surfaces 106 is provided in the internal grip section and extends a distance or height (H) 120 in the longitudinal direction of the main body of the fixture parallel to longitudinal axis 107 of the fixture. The lobe-shaped surfaces 106 may be configured to cooperate with an insertion tool having slightly tapered engaging surfaces to engage and lift the fixture.

Figure 2:
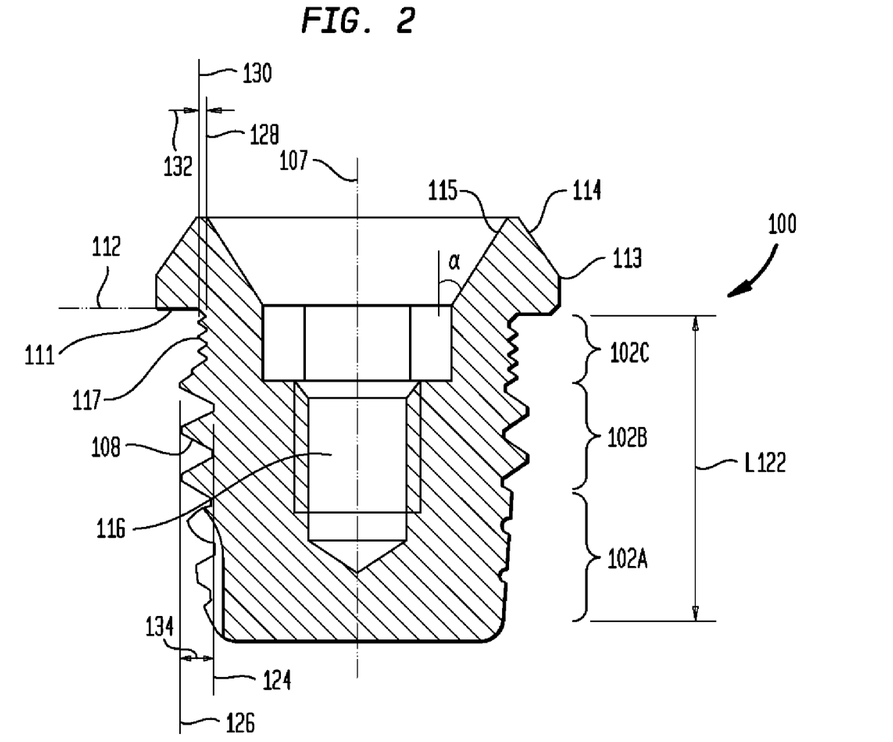
FIG. 2 is a cross-sectional side view of the anchoring element illustrated in FIG. 1.

The main body 102 has a length sufficient to securely anchor fixture 100 into, without penetrating entirely through, the skull bone. The length of main body 102 may therefore depend on the thickness of the skull bone at the implantation site. In one embodiment, main body 102 has a length (L) 122 no greater than approximately 5 mm. Main body 102 further comprises a distal tapered apical portion 102A and a straight, generally cylindrical body comprising two portions, a first portion 102B and a second portion 102C. First portion 102B comprises external threads that form the main screw thread 108 adjacent to the distal tapered apical portion. The second portion 102C is adjacent to the flange. As illustrated in FIG. 2, main screw thread 108 has an inner diameter 124 and an outer diameter 126. In one embodiment, the outer diameter 126 is approximately 3.5-5.0 mm.

As further shown in FIGS. 1 and 2, the distal tapered apical part 102A of main body 102 is configured with self-tapping cutting edges 109. Additional information regarding the self-tapping action is described in greater detail in WO 02/09622, which is hereby incorporated by reference herein. Clearance or relief surfaces 110 may also be provided, wherein the self-tapping cutting edges 109 and the clearance or relief surfaces 110 are provided in an alternating configuration around the main body periphery. This alternating configuration is advantageous because it creates more volume for the cut-off bone chips and therefore reduces the squeezing effect between the fixture 100 and the bone during installation.

As more clearly illustrated in FIG. 2, flange 103 has a planar bottom surface 111 for resting against the outer bone surface, indicated by 112, when the fixture 100 has been screwed into the skull bone. Again, flange 103 prevents the fixture 100 from completely penetrating through the skull bone. Preferably, flange 103 has a diameter which exceeds the peak diameter of the threads by approximately 10-20%. The outer peripheral surface of the flange has a cylindrical part 113 and a tapered top portion 114. The upper end of the flange is designed with an open cavity with a tapered inner side wall 115, a grip section 105, and an inner bottom bore 116 with an internal screw thread for directly or indirectly connecting a hearing aid device or any orbital or ear prosthesis. In order to achieve a stable connection, the inner opening and bore extends to the bottom half of the main body of the fixture 100. The tapered inner side wall 115 forms a seat for a skin-penetrating abutment or the like to create a good connecting fit between the two parts fixture and abutment. The cone angle α may be in the range of about 30-40 degrees. However, the connection with abutment and other parts in the system are not part of this invention and will not be described in any detail here.

In one embodiment, no protruding hex is provided in the embodiment depicted in FIGS. 1 and 2. Rather, the flange forms a smooth, open upper end. The smooth upper end of flange 103 and the absence of any sharp corners provides for improved soft tissue adaptation. Flange 103 also comprises a cylindrical part 113 and a flared top portion 114 which provide sufficient height in the longitudinal direction for internal connection with an abutment sleeve (not shown).

FIG. 2 shows the second portion 102C adjacent to flange 103 having an inner diameter 128 which exceeds the inner diameter 124 of the main threads 108 of the first portion 102B. As noted, this configuration provides a radial compression to the surrounding bone. Preferably the second portion 102C is provided with circumferential grooves 117, having an inner diameter 128 and an outer diameter 130. A drill may then be used having a diameter that is greater than the inner diameter 124 of screw thread 108 of first portion 102B, but less than the outer diameter 130 of second portion 102C of the cylindrical main body of the fixture, that is, 124<Drill Diameter<130. When fixture 100 is inserted into the drilled hole, the second portion 102C compresses the bone to some extent to impart initial stability. The wide diameter portion is located next to the flange so that the compressive action is more concentrated to the hard cortical part of the skull bone tissue.

As mentioned and illustrated in FIGS. 1 and 2, second portion 102C is preferably provided with circumferential grooves 117. In one embodiment, the inner diameter 128 also exceeds the inner diameter 124 of screw thread 108 of first portion 102B. Preferably the height 132 of the groove (130−128=132) is approximately ⅓ or less than the height of screw thread 108 of first portion 102B. In addition to the noted compressive action, such grooves may provide an increased retention between the fixture and the surrounding bone tissue, and spread the forces directed to the abutment more evenly in the bone.

This retention may also be improved by increasing the surface roughness of the bone contacting surfaces of fixture 100. For instance the surface may be modified by means of an abrasive blasting process according to WO 92/05745. In one embodiment the process is used to provide an average surface roughness Sa of about 0.2-2.0 µm, preferably 0.8-1.2 µm, and Sdr(2d/3d)=8-60%, preferably approximately 20-60%.

Circumferentially oriented grooves 117 may extend completely or partly around the periphery of the main body. In the embodiment shown in FIGS. 1 and 2 there are three separate grooves as an example. As an alternative, the grooves may be formed as a screw thread, which may have the same pitch as main screw thread 108, but having a inner diameter 128 that is greater than the inner diameter 124 of main screw thread 108, so that the height of the grooves 117 would be only approximately ⅓ or less of the height 134 of main screw thread 108 (126−124=134). In one embodiment, the extension of the second wide diameter portion 102C in the longitudinal direction of the fixture is about 15-25% of the total height of the fixture.

A method for inserting the fixture may comprise providing the anchoring fixture, drilling a hole, and inserting the anchoring fixture into the hole until the flange contacts the skull bone, wherein the hole has a diameter that is greater than the inner diameter of the first portion and less than the outer diameter of the second portion. No countersinking or removal of cortical bone is used which leaves more good bone left. When fixture 100 is inserted into such a drilled hole, the wider second portion of the fixture, that is, portion 102C next to the flange, provides a certain compression of the cortical bone on the radial direction of the prepared bone hole.

Further features and advantages of the present invention may be found in U.S. Provisional Application No. 60/951,169, entitled "Coupling Apparatus For a Bone Anchored Hearing Device," and filed Jul. 20, 2007, and U.S. Provisional Application No. 60/951,163, entitled "Bone Anchor Fixture for a Medical Prosthesis," and filed Jul. 20, 2007, which are hereby incorporated by reference herein.

The invention is not limited to the embodiment illustrated in the drawings but may be varied within the scope of the accompanying claims. Specifically, it is understood that other types of abrasive methods, coatings etc, may be used for increasing the roughness of bone-contacting surfaces. Such methods are known per se and not described here in any detail.

What is claimed is:

1. An anchoring fixture for anchoring a prosthesis to a skull bone comprising:
   a screw thread apparatus including a screw thread having a varying outer diameter; and
   a protrusion configured to prevent the anchoring fixture from completely penetrating through a skull of a human, wherein
   a portion of a surface of the anchoring fixture that contacts the skull bone has a modified increased surface roughness relative to another portion of the surface of the anchoring fixture that contacts the skull bone, and
   the anchoring fixture is configured for anchoring a hearing prosthesis component to the skull bone at a location behind an external ear so that sound is transmitted from the hearing prosthesis via the skull bone to a cochlea, wherein:
   a maximum diameter of the screw thread apparatus is between 3.5 and 5 mm;
   a length from a bottom of the protrusion to a distal end of the anchoring fixture is no greater than 5 mm, the screw thread apparatus and the distal end being on a same side of the protrusion;
   a maximum diameter of the protrusion is greater than the length from the bottom of the protrusion to the distal end of the anchoring fixture; and
   the maximum diameter of the protrusion has a value that exceeds a peak diameter of the screw thread by approximately 10-20%.

2. The anchoring fixture of claim 1, wherein:
   a distance from the protrusion to the distal end of the anchoring fixture is completely threaded.

3. The anchoring fixture of claim 1, wherein:
   the protrusion includes a cylindrical portion and a horizontal stop surface is formed on an underside of the cylindrical portion.

4. The anchoring fixture of claim 1, wherein:
   the anchoring fixture has a first section between, with respect to location along a longitudinal axis of the anchoring fixture, a surface of the protrusion that extends normal to the longitudinal axis and is configured to abut the skull bone and at least a portion of the screw thread; and
   at least one of:
      the first section is different from a section that establishes the screw thread apparatus in that the first section includes a circumferential valley between a beginning of the screw thread and an end of the protrusion;
      the first section establishes a grooved region, and establishes one single grooved region that is the only grooved region between the protrusion and the distal end of the anchoring fixture; or
      the first section is different from the section that establishes the screw thread apparatus and overlaps with the section that establishes the screw thread apparatus.

5. The anchoring fixture of claim 1, wherein:
   a portion of the anchoring fixture between the protrusion and the distal end of the anchoring fixture has a wide diameter portion located next to the protrusion so that a compressive action is more concentrated to a hard cortical part of tissue of the skull bone when fully seated in the skull bone.

6. The anchoring fixture of claim 1, wherein:
   the anchoring fixture includes a tapered portion that establishes a seat for a skin-penetrating abutment to create a connecting fit between the anchoring fixture and the abutment.

7. The anchoring fixture of claim 1, wherein:
   the anchoring fixture has a first section, with respect to location along a longitudinal axis of the anchoring fixture, between a surface of the protrusion that extends normal to the longitudinal axis and is configured to abut the skull bone and at least a portion of the screw thread; and
   the first section includes a space in the form of a valley that is not threaded.

8. A bone fixture configured to anchor to bone, comprising:
a threaded portion; and
a first surface located above the threaded portion and extending outward past all threads of the bone fixture, wherein
the bone fixture is configured to anchor a hearing aid prosthesis to a skull bone at a location behind an external ear of a recipient so that sound is transmitted from the hearing prosthesis via the skull bone to a cochlea,
the threaded portion is at least bifurcated into two sections, a first section where thread thereof has a maximum outer thread radius as measured from a longitudinal axis of the bone fixture that is less than that of a second section immediately adjacent the first section, and
a portion of a thread that is at least part of the first section has at least a crest that only extends partially about the periphery of the bone fixture.

9. The bone fixture of claim 8, wherein:
the second section has at least four turns of the thread that have a maximum outer thread radius as measured from the longitudinal axis of the bone fixture that is greater than that of the first section.

10. The bone fixture of claim 8, wherein:
an inner diameter of the thread of the first section is greater than an inner diameter of at least some of the thread of the second section.

11. The bone fixture of claim 8, wherein:
the threaded portion has a screw thread maximum diameter that decreases with location along the longitudinal axis of the bone fixture, which decrease is non-linear.

12. The bone fixture of claim 8, wherein the bone fixture comprises a wide portion that is located, with respect to a side of the first surface, on a threaded side of the bone fixture, wherein the wide portion is configured to exert a compression onto the skull bone in a radial direction, to stabilize the bone fixture in the skull bone, when the bone fixture is implanted.

13. The bone fixture of claim 8, wherein:
the bone fixture includes a circumferential sideways V shaped outer boundary of a cross-section taken parallel to the longitudinal axis of the bone fixture and lying on the longitudinal axis on either side of the longitudinal axis, the V shaped outer boundary being between a portion of the thread that is at least part of the first section and the first surface, the V forming a minimum inner diameter that is greater than a plurality of inner diameters of respective turns of the thread that is at least part of the first section.

14. An anchoring fixture comprising:
a main body having a screw thread having a varying outer diameter; and
a head adjacent the main body, the head configured to function as a screw head with respect to depth positioning relative to a surface of a skull bone, wherein
the anchoring fixture is configured to anchor a hearing prosthesis to the skull bone at a location behind an external ear so that vibrations based on sound are transmitted from the hearing prosthesis via the skull bone to a cochlea in a recipient of the anchoring fixture, and
a maximum diameter of the screw thread is greater than a length from a bottom of the head to a distal end of the anchoring fixture.

15. The anchoring fixture of claim 14 wherein:
the anchoring fixture has a first section between, with respect to location along a longitudinal axis of the anchoring fixture, a surface of the head that extends normal to the longitudinal axis and is configured to abut the skull bone and at least a portion of the screw thread;
the first section is different from a section of the anchoring fixture including the screw thread; and
there is no distinct region separating the first section from the section of the anchoring fixture including the screw thread.

16. The anchoring fixture of claim 14, wherein:
the anchoring fixture has a first section between, with respect to location along a longitudinal axis of the anchoring fixture, a surface of the head that extends normal to the longitudinal axis and is configured to abut a top surface of the skull bone and at least a portion of the screw thread;
the anchoring fixture includes a threaded section including the screw thread;
the anchoring fixture includes a head section including the head;
the only section between the head section and the threaded section is the first section which is a non-threaded section; and
a non-helixed valley extends about the anchoring fixture and is located between the screw thread and the surface of the head.

17. The anchoring fixture of claim 14, wherein:
the anchoring fixture has a surface feature that changes with respect to location along a longitudinal axis of the anchoring fixture, between a surface of the head that extends normal to the longitudinal axis and is configured to abut a top surface of the skull bone and at least a portion of the thread, the surface feature that changes being a distance from the surface and the longitudinal axis; and
a minimum distance from the surface and the longitudinal axis is greater than an inner diameter of the screw thread.

18. The anchoring fixture of claim 14, wherein:
the anchoring fixture has a groove; and
an inner diameter of a surface that establishes the groove is greater than an inner diameter of the screw thread along the entire length of the anchoring fixture.

19. The anchoring fixture of claim 14, wherein:
the anchoring fixture has a first section between, with respect to location along a longitudinal axis of the anchoring fixture, a surface of the head that extends normal to the longitudinal axis and is configured to abut the skull bone and at least a portion of the screw thread; and
the only thing between an end of the screw thread and the surface of the head is the first section, wherein the first section consists of a first sub-section and a second sub-section, the first sub-section is immediately adjacent the screw thread and the second sub-section is immediately adjacent the first sub-section, wherein the second sub-section includes an outwardly tapered portion that extends towards the surface of the head, and wherein the first-sub section is a geometry that transitions from the second-sub section and the screw thread.

20. The bone fixture of claim 8, wherein:
the bone fixture includes a valley between the portion of the screw thread that is at least part of the first section and the first surface, the valley having a minimum inner diameter that is greater than a plurality of inner diameters of respective turns of the screw thread that is at least part of the first section.

21. The anchoring fixture of claim 1, wherein:
the anchoring fixture has a groove; and
a minimum inner diameter of the groove is greater than a maximum inner diameter of the screw thread and a maximum outer diameter of the groove is less than a maximum outer diameter of the screw thread.

22. The anchoring fixture of claim 1, wherein:
a bottom of the protrusion has a planar surface.

23. The anchoring fixture of claim 1, wherein:
a bottom of the protrusion has a planar surface and, relative to a longitudinal axis of the anchoring fixture, an oblique surface.

24. The anchoring fixture of claim 1, wherein:
a bottom surface of the protrusion is planar and functions as a stop for the anchoring fixture and is adapted to rest on top of the bone when the anchoring fixture is implanted into the skull bone.

25. The anchoring fixture of claim 1, wherein:
the protrusion is a flange.

26. The anchoring fixture of claim 1, wherein:
a bottom portion of the protrusion facing the distal end has a surface that is oblique to a longitudinal axis of the anchoring fixture.

27. The anchoring fixture of claim 1, wherein:
a surface of a bottom of the protrusion on a side of the protrusion closer to the distal end relative to an opposite side of the protrusion has a surface that is oblique to a longitudinal axis of the anchoring fixture.

28. The anchoring fixture of claim 1, wherein:
the protrusion extends completely about a longitudinal axis of the anchoring fixture.

29. The anchoring fixture of claim 1, wherein:
the protrusion is a circular projection.

30. The anchoring fixture of claim 1, wherein:
the protrusion is a flange, and a bottom of the protrusion has a planar surface and, relative to a longitudinal axis of the anchoring fixture, an oblique surface.

31. The anchoring fixture of claim 1, wherein:
the anchoring fixture has a groove; and
a minimum inner diameter of the groove is greater than a maximum inner diameter of the screw thread and a maximum outer diameter of the groove is less than a maximum outer diameter of the screw thread.

32. The bone fixture of claim 8, wherein:
the bone fixture is configured such that the first surface rests on top of bone when the bone fixture is implanted into the skull bone.

33. The bone fixture of claim 8, further comprising:
a second surface adjacent and oblique to the first surface, the second surface facing the skull bone when the bone fixture is anchored to bone.

34. The bone fixture of claim 8, further comprising:
a second surface adjacent and oblique to the first surface; and
a third surface oblique to the second surface and outboard of the second surface and the first surface, the third surface establishing an outermost surface of the bone fixture relative to distance from the longitudinal axis of the bone fixture.

35. The bone fixture of claim 8, wherein:
the bone fixture is established by a main body and a head body;
the main body establishes the threaded portion;
the head body establishes the first surface, a second surface adjacent and oblique to the first surface, and a third surface oblique to the second surface and outboard of the second surface and the first surface; and
the third surface establishes an outermost periphery of the head body and is parallel to the longitudinal axis.

36. The bone fixture of claim 35, wherein:
the head body establishes a stop for the bone fixture with respect to depth of insertion of the bone fixture into bone.

37. The bone fixture of claim 8, further comprising:
a second surface adjacent and oblique to the first surface; and
a third surface adjacent and oblique to the second surface, the third surface establishing an outermost surface of the bone fixture relative to distance from a longitudinal axis of the bone fixture, the first surface being normal relative to the longitudinal axis, the third surface being parallel to the longitudinal axis.

38. The bone fixture of claim 8, wherein:
the first surface is part of a flange of the bone fixture.

39. The bone fixture of claim 37, wherein:
the first surface, the second surface and the third surface are part of a flange of the bone fixture.

40. The bone fixture of claim 8, wherein:
the first surface is part of a bottom of a flange of the bone fixture that is a planar surface; and
the bottom further includes a second surface that extends in a lateral direction and a longitudinal direction.

41. The bone fixture of claim 8, wherein:
the first surface is part of a bottom of a flange of the bone fixture that is a planar surface, and wherein the bottom further includes a second surface that extends obliquely away from the first surface.

42. The bone fixture of claim 35, wherein:
the third surface is parallel to the longitudinal axis.

43. The bone fixture of claim 8, wherein:
the bone fixture has a groove; and
a minimum inner diameter of the groove is greater than a maximum inner diameter of screw thread of the threaded portion and a maximum outer diameter of the groove is less than a maximum outer diameter of the screw thread of the threaded portion.

44. The anchoring fixture of claim 14, wherein:
a bottom surface of the head has a planar surface.

45. The anchoring fixture of claim 14, wherein:
a bottom surface of the head has a planar surface; and
a bottom surface of the head is oblique relative to a longitudinal axis of the anchoring fixture.

46. The anchoring fixture of claim 14, wherein:
a bottom surface of the head is oblique relative to a longitudinal axis of the anchoring fixture.

47. The anchoring fixture of claim 14, wherein:
a portion of the head on a side of the head closer to the distal end of the anchoring fixture than an opposite side of the head is bounded by a compound face extending from the main body to a surface that establishes an outermost periphery of the head.

48. The anchoring fixture of claim 14, wherein:
a cross-section of the anchoring fixture lying on a plane that is on a longitudinal axis of the anchoring fixture and parallel thereto has an outer profile that extends from a boundary of the main body to an outermost profile, relative to the longitudinal axis, of the head, the outer profile being a compound profile.

49. The anchoring fixture of claim 14, wherein:
a cross-section of the anchoring fixture lying on a plane that is on a longitudinal axis of the anchoring fixture and parallel thereto has a segment between an outermost profile, relative to the longitudinal axis, of the head, extending towards the longitudinal axis, that has a portion that is straight and normal to the longitudinal axis and a portion that is straight and oblique relative to the longitudinal axis.

50. The anchoring fixture of claim 14, wherein:
the anchoring fixture has a groove; and
a minimum inner diameter of the groove is greater than a maximum inner diameter of the screw thread and a maximum outer diameter of the groove is less than a maximum outer diameter of the screw thread.

51. The anchoring fixture of claim 14, further comprising:
a circumferential groove, wherein the circumferential groove is separate from the screw thread of the main body.

52. The anchoring fixture of claim 14, further comprising:
a circumferential groove, wherein the circumferential groove is coaxial with the main body.

53. The bone fixture of claim 8, further comprising:
a circumferential groove, wherein the circumferential groove is coaxial with a head of the bone fixture.

54. The anchoring fixture of claim 14, wherein:
the anchoring fixture includes a threaded section including the screw thread;
the head includes a surface that extends normal to a longitudinal axis of the anchoring fixture and is configured to abut the skull bone; and
at least one of:
  (i) there is no distinct region separating the threaded section from the head;
  (ii) there is no distinct region separating the threaded section from the surface of the head, and a groove is located between the screw thread and surface of the head;
  (iii) the threaded section is immediately adjacent to the surface of the head; or
  (iv) the threaded section is immediately adjacent to the surface of the head and a groove is located between the screw thread and the surface of the head.

55. The anchoring fixture of claim 14, wherein:
the screw thread includes an inner diameter that remains about constant over at least most of the length of the screw thread.

56. The bone fixture of claim 8, wherein:
the bone fixture comprises a material configured to integrate into surrounding bone tissue.

57. The bone fixture of claim 8, wherein:
a thread pitch of the first section is the same as that of the second section.

58. The bone fixture of claim 8, wherein:
a thread pitch of the first section is not the same as that of the second section.

59. The bone fixture of claim 8, wherein:
a cross-section of the bone fixture lying on and parallel to the longitudinal axis of the bone fixture has, on one side, with respect to location from a proximal end to a distal end of the bone fixture, starting at a location of maximum screw thread radius on the one side, six turns inclusive of the turn having the maximum screw thread radius.

60. The bone fixture of claim 8, wherein:
with respect to location from a proximal end to a distal end of the bone fixture, starting at a location of maximum screw thread radius of the threaded portion, the height of the thread decreases.

61. The anchoring fixture of claim 14, wherein:
the anchoring fixture has a surface that has a surface feature that changes with respect to location along a longitudinal axis of the anchoring fixture, between a surface of the head that extends normal to the longitudinal axis and is configured to abut a top surface of bone of the skull bone and at least a portion of the screw thread, the surface feature that changes being a distance from the surface of the anchoring fixture and the longitudinal axis, which distance is normal to the longitudinal axis; and
a minimum distance from the surface of the anchoring fixture and the longitudinal axis is greater than an inner diameter of the screw thread at a tapered portion of the anchoring fixture, which minimum distance is normal to the longitudinal axis.

* * * * *